United States Patent
Helfer et al.

(10) Patent No.: US 6,925,322 B2
(45) Date of Patent: Aug. 2, 2005

(54) OPTICAL MRI CATHETER SYSTEM

(75) Inventors: Jeffrey L. Helfer, Webster, NY (US); Stuart G. MacDonald, Pultneyville, NY (US); Robert W. Gray, Rochester, NY (US); Christopher Thomas, Rochester, NY (US)

(73) Assignee: Biophan Technologies, Inc., West Henrietta, NY (US)

( * ) Notice: Subject to any disclaimer, the term of this patent is extended or adjusted under 35 U.S.C. 154(b) by 466 days.

(21) Appl. No.: 10/202,921

(22) Filed: Jul. 25, 2002

(65) Prior Publication Data

US 2004/0019273 A1 Jan. 29, 2004

(51) Int. Cl.[7] .............................. A61B 5/05; A61B 6/00
(52) U.S. Cl. ....................... 600/423; 600/433
(58) Field of Search ................. 600/423, 425, 600/422, 417, 407, 421, 410, 414, 433, 585; 324/318, 307, 308, 309

(56) References Cited

U.S. PATENT DOCUMENTS

| | | | | |
|---|---|---|---|---|
| 5,882,305 A | * | 3/1999 | Dumoulin et al. | 600/421 |
| 6,493,573 B1 | * | 12/2002 | Martinelli et al. | 600/424 |
| 6,535,755 B2 | * | 3/2003 | Ehnholm | 600/423 |
| 6,537,232 B1 | * | 3/2003 | Kucharczyk et al. | 600/561 |
| 6,584,343 B1 | * | 6/2003 | Ransbury et al. | 600/509 |
| 6,636,757 B1 | * | 10/2003 | Jascob et al. | 600/424 |

* cited by examiner

Primary Examiner—Daniel Robinson
(74) Attorney, Agent, or Firm—Howard J. Greenwald; John M. Hammond

(57) ABSTRACT

An assembly for delivering optical signals that has a nuclear magnetic resonance system, an optical interface assembly, and a catheter assembly with a fiber optic cable assembly and an optical interface and an antenna. The catheter assembly converts electromagnetic signals received by the antenna into optical signals. The optical interface assembly converts optical signals into electrical signals and electrical signals into optical signals.

42 Claims, 9 Drawing Sheets

OPTICAL MRI CATHETER SYSTEM

FIELD OF THE INVENTION

An invasive apparatus for receiving a magnetic resonance signal from within a body and providing means for transmitting the signal to the received signal input channel of standard magnetic resonance systems.

BACKGROUND OF THE INVENTION

Magnetic resonance imaging ("MRI") has been developed as an imaging technique adapted to obtain both images of anatomical features of human patients as well as some aspects of the functional activities and characteristics of biological tissue. These images and/or functional and/or chemical measurements have medical diagnostic value in determining the state of the health of the tissue examined.

In an MRI process, a patient is typically aligned to place the portion of the patient's anatomy to be examined in the imaging volume of the MRI apparatus. Such an MRI apparatus typically comprises a primary magnet for supplying a constant magnetic field ($B_0$) which, by convention, is along the z-axis and is substantially homogeneous over the imaging volume and secondary magnets that can provide linear magnetic field gradients along each of three principal Cartesian axes in space (generally x, y, and z, or $x_1$, $x_2$ and $x_3$, respectively). A magnetic field gradient ($\Delta B_0/\Delta x_1$) refers to the variation of the field along the direction parallel to $B_0$ with respect to each of the three principal Cartesian axes, $x_1$. The apparatus also comprises one or more RF (radio frequency) coils which provide excitation and detection of the MRI signal. Additionally or alternatively, detection coils may be designed into the distal end of a catheter to be inserted into a patient. When such catheters are employed, their proximal ends are connected to the received signal input channel of the magnetic resonance imaging device. The detected signal is transmitted along the length of the catheter from the receiving antenna and/or receiving coil in the distal end to the MRI input channel connected at the proximal end.

The insertion of metallic wires into a body, e.g. catheters and guidewires, while in a magnetic resonance imaging environment, poses potentially deadly hazards to the patient through excessive heating of the wires, e.g. in excess of 74° C. in some studies. M. K. Konings, et. al, in "Catheters and Guidewires in Interventional MRI: Problems and Solutions", MEDICA MUNDI 45/1 March 2001, list three ways in which conductors may heat up in such environments: 1) eddy currents, 2) induction loops, and 3) resonating RF transverse electromagnetic (TEM) waves along the length of the conductors. They write: "Because of the risks associated with metal guidewires, and catheters with metal conductors, in the MRI environment, there is an urgent need for a non-metallic substitute, both for guidewires and for signal transfer." They further propose the use of " . . . a full-glass guidewire with a protective polymer coating . . . . "

The tracking and placement of a catheter within a body is an important aspect of using catheters in magnetic resonance imaging procedures. Considering the dangers inherent in the use of metallic wires in the magnetic resonance imaging environment, as mentioned above, M. K. Konings, et. al., in their paper "Development of an MR-Safe Tracking Catheter With a Laser-Driven Tip Coil" describe the design of a tracking catheter " . . . using an optical fiber with a light-diffusing tip segment to transport laser energy through the catheter. This energy is converted to a DC current running through a small coil at the catheter tip. Our method is inherently MR-safe since the use of long conducting wires is avoided."

From the paper "An Optical System for Wireless Detuning of Parallel Resonant Circuits" by E. Y. Wong, et. al., in the Journal of Magnetic Resonance Imaging 12:632–638 (2000), it is pointed out that typically when a catheter coil is used in magnetic resonance imaging, it is necessary to detune the coil away from the frequency of the magnetic resonance imaging system during the transmission of the magnetic resonance imaging pulse sequence. The authors write "In all MRI experiments in which local coils are used for signal reception, coil detuning is necessary during transmission to prevent high voltages from being induced in the receiver coil and other electronic components including the receiver preamplifier. The potentially high voltages and currents, as well as the induced electric fields, pose a safety hazard for the patient, . . . , and disrupt the desired uniform excitation field generation required for excitation; this may lead to particular localized effects in interventional or intravascular MR imaging in which small coils are used." This paper further describes the use of a complex design consisting of fiber optic cable and photoresistors to overcome these problems.

By providing a catheter with an MR receiving coil or antenna in the distal end, the coil or antenna can be placed closer to the tissue which is to be imaged or analyzed. Thus the detected signal is less susceptible to radio frequency noise. Additionally, the level of detail that can be resolved (the resolution of the image, spectrum, or other data obtained) is increased by the use of catheter coils.

Thus, it is desirable to provide an apparatus such as a catheter which can be used with a magnetic resonance system for insertion and positioning of an magnetic resonance receiver coil or antenna within a body which is not susceptible to the heating, noise pickup, electrostatic buildup and/or other hazards associated with the use of conductors in a magnetic resonance environment.

SUMMARY OF THE INVENTION

In accordance with this invention, there is provided an apparatus for use in a magnetic resonance environment, comprised of a fiber optic cable assembly comprised of a distal end with detection coils or antenna with signal transductance means and comprised of a proximal end with an adaptor component with signal transductance means suitable for connection to a standard receiver input channel of a magnetic resonance system.

BRIEF DESCRIPTION OF THE DRAWINGS

The invention will be described by reference to the following drawings, in which like numerals refer to like elements, and in which.

DESCRIPTION OF THE PREFERRED EMBODIMENTS

Figure 1:
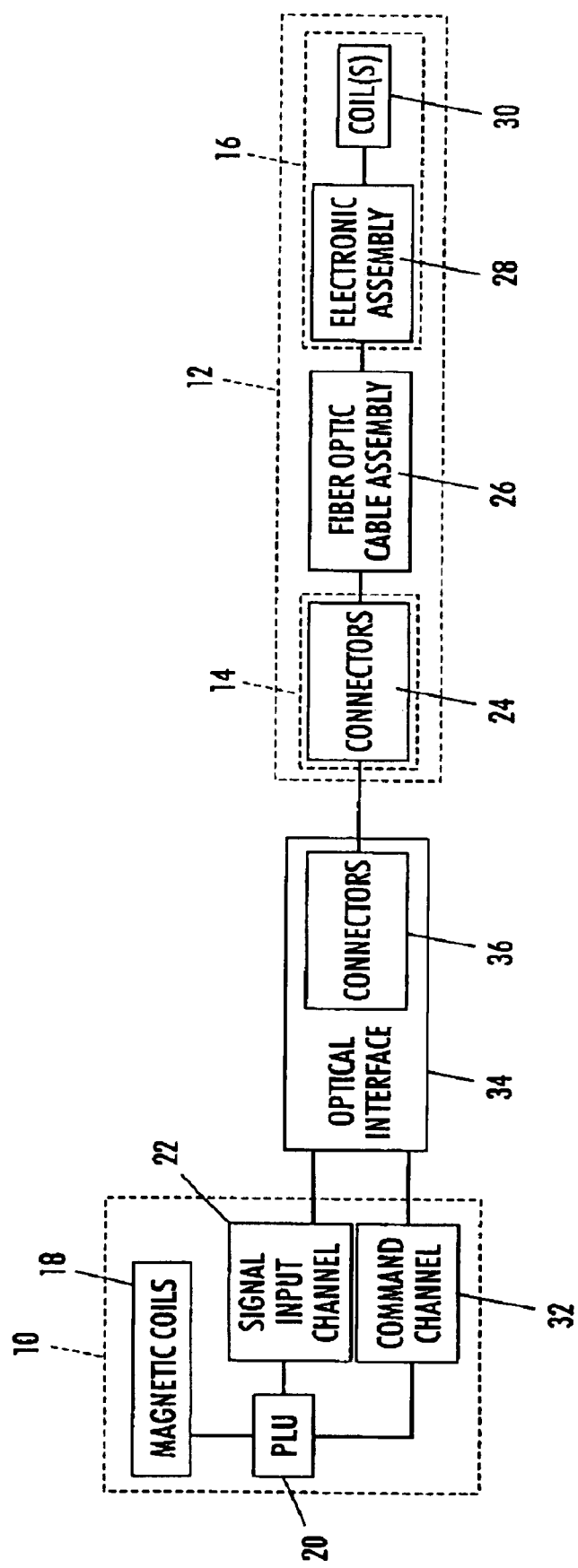
FIG. 1 is a block diagram of one preferred apparatus of the invention.

In one embodiment, the apparatus of this patent application comprises the structure shown in FIG. 1. Referring to FIG. 1, a standard magnetic resonance system 10 (e.g. the GE Signa Infinity 1.5 Tesla system, or Siemens Symphony 1.5 Tesla system) comprises means for generating and controlling magnetic fields 18, which may comprise electromagnets and/or permanent magnets, a programmable logic unit 20, a receiver input channel 22 and a command/gating output channel 32. The receiver input channel 22 is used to pass the detected signals to the programmable logic unit for image reconstruction. The command/gating output channel 32 is used to provide at minimum gating signals synchronized to the application of the gradient magnetic fields of the magnetic resonance system 10.

Continuing to refer to FIG. 1, and to the embodiment depicted therein, an optical interface assembly 34 is connected to the receiver input channel 22 and to the command/gating output channel 32 of the magnetic resonance system 10. The optical interface assembly 34 converts the electrical command/gating signals of the magnetic resonance system 10 issued through the command/gating output channel 32 into optical signals and transmits these optical signals through the catheter assembly 12. The optical interface assembly 34 also converts the optical signals received from the catheter 12 into electrical signals suitable for the magnetic resonance system's 10 receiver input channel 22.

Continuing to refer to FIG. 1, the optical interface assembly 34 is connected to the catheter assembly 12 through optical connector assembly 36 within the optical interface assembly 34 and optical connector assembly 24 in the proximal end 14 of the catheter assembly 12. Optical connectors are well known to those skilled in the arts. Reference may be had, e.g., to U.S. Pat. No. 6,149,313 (Gender selectable fiber optic connector and associated fabrication method ), which discloses "A gender selectable fiber optic connector is provided which can be readily converted between male and female configurations following assembly and polishing of the connector." U.S. Pat. No. 5,619,605 (Optical connector) discloses "A novel optical connector that includes the following: an optical connector ferrule which is capable of fixing optical fibers; optical fibers fixed onto the optical connector ferrule, such that the end surfaces of the optical fibers project beyond an end surface of the optical connector ferrule; an adhesive for fixing the optical fibers onto the optical connector ferrule; and a member whose Young's Modulus is less than that of the optical fiber and is provided to an area on the end surface of the optical connector ferrule surrounding, at a minimum, the projected portions of the optical fibers." Further reference may be had to U.S. Pat. No. 4,934,785 (Optical fiber connector), U.S. Pat. No. 5,963,690 (Optical fiber connector), U.S. Pat. No. 6,367,984 (Optical fiber adapter), U.S. Pat. No. 6,179,482 (Optical connector and housing for optical connector), U.S. Pat. No. 5,590,227 (Optical connector apparatus), U.S. Pat. No. 5,214,730 (Multifiber optical connector plug with low reflection and low insertion loss). The entire disclosure of each of these United States patents is hereby incorporated by reference into this specification.

Referring again to FIG. 1, the optical connector assembles 36, 24 may be so constructed as to allow the catheter assembly 12 to be detached from the optical interface assembly 34. Reference may be made to U.S. Pat. No. 5,631,988 (Parallel optical interconnect) which discloses "An optical interconnect is disclosed that couples multiple optical fibers to an array of optoelectronic devices. The interconnect includes a multiple optical fiber connector and an optoelectronic board. The multiple fiber connector can be mechanically attached to or detached from the board." U.S. Pat. No. 4,804,244 (Connector for optical fiber) discloses "An optical fiber connector in which an optical fiber and an optical conversion element are detachably coupled together, and optical fibers are mutually coupled together." The entire disclosure of each of these United States patents is hereby incorporated by reference into this specification.

Continuing to refer to FIG. 1, the optical connectors 24 are fabricated to one end of the fiber optic cable assembly 26. The fiber optical cable assembly 26 may comprise one or more fiber optical strands suitable for transmitting optical signals from the distal end 16 of the catheter assembly 12 to the proximal end 14 of the catheter assembly 12. Such fiber optic cable assembly 26 is typical of prior art optical cable assemblies. Reference may be had, e.g., to U.S. Pat. No. 4,784,461 (optical cable with improved strength), U.S. Pat. No. 6,259,843 (optical cable), U.S. Pat. No. 5,611,016 (dispersion balanced optical cable), U.S. Pat. No. 4,911,525 (optical communications cable), U.S. Pat. No. 4,798,443 (optical cable), U.S. Pat. No. 5,634,720 (multi-purpose multi-parameter cardiac catheter), and the like. The entire disclosure of each of these United States patents is hereby incorporated by reference into this specification.

Additionally, fiber optic cable assembly 26 may comprise one or more lumens (not shown) suitable for the transport of a gas, e.g., air, or a liquid, e.g., a soluble drug in a saline or other solution, through the length of the catheter assembly 12. Additionally, said lumens (not shown), may allow a flexible solid material, e.g. a flexible plastic rod, to be maneuvered through the length of the catheter assembly 12. Such lumens (not shown) are well known to those skilled in the arts of catheter assemblies and are typically used to extend or retract position stabilizing balloons (not shown) or other position stabilizing means built into the catheter assembly 12. Additionally, said lumens (not shown) are used for performing biopsies, delivering stunts, delivering drugs, and/or for other therapeutic purpose and/or medical procedures. Such lumens may be made from nonconductive, nonmagnetic material, e.g. plastics, or silicon dioxide, etc. Reference to such catheter assemblies may be made to International patent publication PCT WO 01/74241 A2 (Systems And Methods For Evaluating The Urethra And The Periurethral Tissues), U.S. Pat. No. 6,056,721 (Balloon catheter and method), U.S. Pat. No. 5,575,772 (Albation catheters), U.S. Pat. No. 6,146,415 (Stent delivery system), and the like. The entire disclosure of each of these United States patents is hereby incorporated by reference into this specification.

Continuing to refer to FIG. 1 and the embodiment depicted therein, the fiber optical cable assembly 26 is connected to an electronic assembly 28 within the distal end 16 of the catheter assembly 12. The electronic assembly 28 provides the means for converting the electrical signal received by the pickup coil(s) 30 into an optical signal and to transmit said optical signal through the fiber optic cable assembly 26 to the proximal end 14 of the catheter assembly 12. Additionally, electronic assembly 28 may receive optically encoded command/gating signals which originate as electrical signals from the magnetic resonance system's 10 command/gating output channel 32, which are converted to optical command/gating signals in the optical interface 34.

Said command/gating signals may be used by the electronic assembly 28 to, e.g. select which of several receiver coils 30 is to be utilized, tune and/or detune receiver coils 30 into or away from a frequency range, activate a gating switch connected to receiver coils 30, etc. Additionally or alternatively, said optical command/gating signals may be converted in total or in part into electrical power in the electronic assembly 28.

Continuing to refer to FIG. 1, the receiving catheter coils 30 may be any one of or a multiplicity of several coils and/or antenna used to receive signals from the tissues that have been excited by the magnetic resonance system 10. Various catheter coil designs are well known to those skilled in the arts. Reference may be had to, e.g., U.S. Pat. No. 6,263,229 (Miniature Magnetic Resonance Catheter Coils and Related Methods) which discloses "The present invention provides several embodiments of methods of making magnetic resonance catheter coils which include employing a flexible electrically insulative base member, depositing an electrically conductive material on the base member in a predetermined pattern to create at least one pair of generally parallel electrically conductive coil elements which are electrically connected to each other." U.S. Pat. No. 5,928,145 (Method of magnetic resonance imaging and spectroscopic analysis and associated apparatus employing a loopless antenna) discloses "The invention provides a method for magnetic resonance imaging and spectroscopic analysis of a specimen which includes positioning the specimen within a main magnetic field and introducing an antenna having a loopless antenna portion in close proximity to the specimen." U.S. Pat. No. 5,699,801 (Method of internal magnetic resonance imaging and spectroscopic analysis and associated apparatus) discloses "The invention provides a method for magnetic resonance imaging and spectroscopic analysis of the interior of a specimen which includes positioning the specimen within a main magnetic field, introducing an invasive probe having an elongated receiver coil into or adjacent to the specimen with the coil having at least one pair of elongated electrical conductors, preferably, generally parallel to each other disposed within a dielectric material and having a pair of ends electrically connected to each other. RF pulses are provided to the region of interest to excite magnetic resonance signals, gradient magnetic pulses are applied to the region of interest with the receiver coil receiving magnetic resonance signals and emitting responsive output signals which may be processed by a computer to provide image information for display in a desired manner." The entire disclosure of each of these United States patents is hereby incorporated by reference into this specification.

Figure 2:
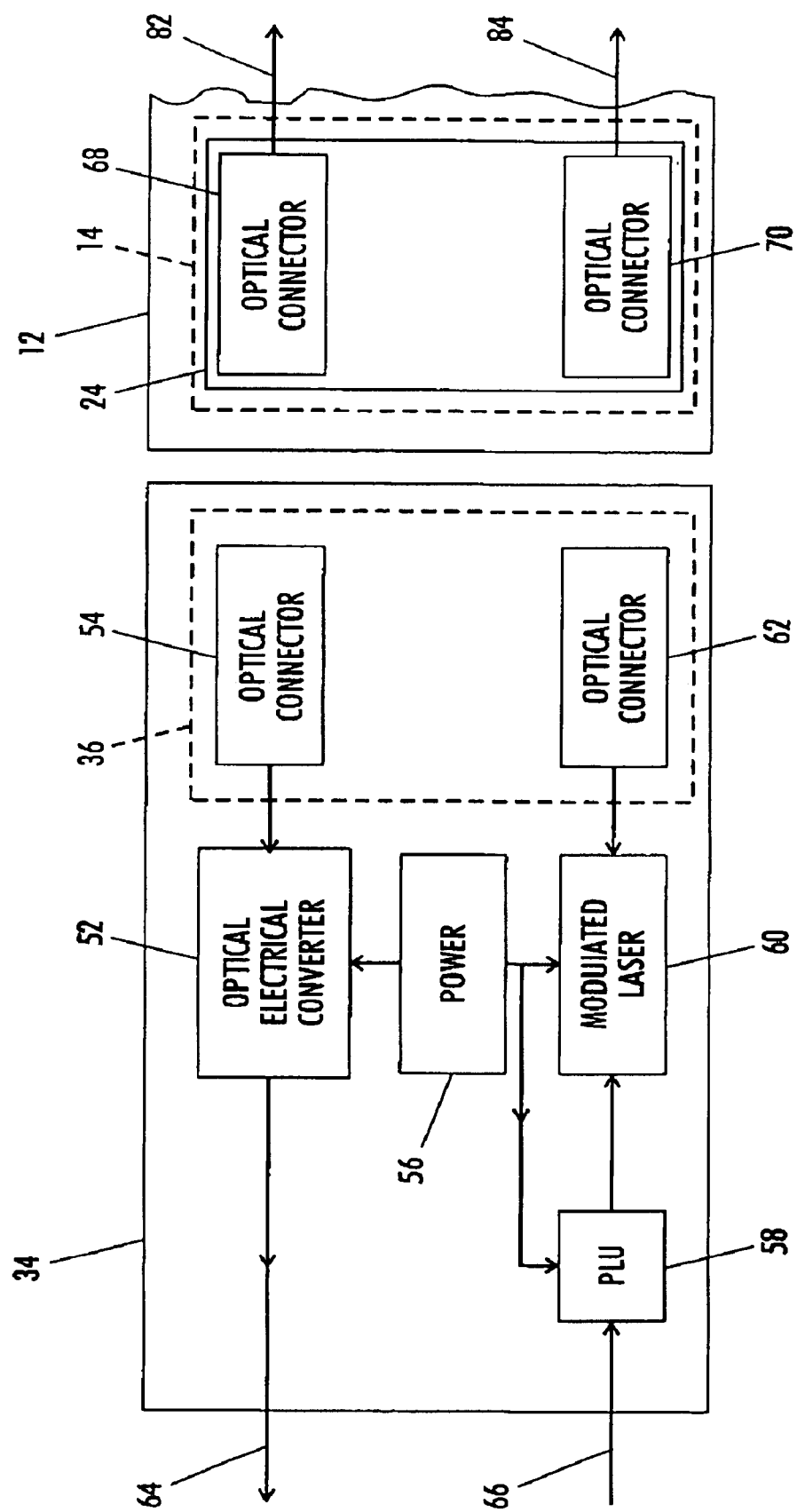
FIG. 2 is a block diagram of the Optical Interface component of the device of FIG. 1.

FIG. 2 is a schematic of an optical interface assembly 34 that may be used in the device of FIG. 1. Referring to FIG. 2, it will be seen that optical connectors 54 and 62 of the optical interface assembly 34 are the mating connectors to connectors 68 and 70. Connectors 68 and 70 comprise the proximal end 14 connector assembly 24 of the catheter assembly 12. The proximal ends of the fiber optic strands 82, 84 are connected to the optical connectors 68 and 70. Optical connectors 54, 62, 68, 70 may be, e.g., Tyco Electronic's AMP Ceramic style ST Connector part number 502579-2 or Tyco Electronic's AMP Ceramic style FC Connector Part number 504649-2. In this embodiment, optical connectors 54 and 62 comprise the connector assembly 36 of FIG. 1. Optical connector 54 is used to receive optical signals from the catheter assembly 12. Optical connector 62 is used to send optical signals through the catheter assembly 12.

Continuing to refer to FIG. 2 and to the embodiment depicted therein, the connection lines 64 and 66 are used to connect the optical interface assembly 34 to the magnetic resonance system's (10 of FIG. 1) signal input channel 22 of FIG. 1 and to the command/gating output channel 32 of FIG. 1 respectively. The connection line 64 is connected to the optical to electrical signal converter 52 component of the optical interface assembly 34. Optical to electrical signal converter 52 may be, e.g., a standard photodiode operating in a photoconductive mode. One such photodiode is UDT Sensors Inc.'s High Speed Silicon Fiber Optic Detector, part number PIN-HR020. In another preferred embodiment (not shown), optical to electrical signal converter 52 comprises electrical amplification means (not shown), e.g. an operational amplifier, and other electronic components (not shown) suitable for reproducing the original electrical signal and for matching the impedance and/or other electrical characteristics of the signal input channel 22 of FIG. 1 of the magnetic resonance system 10 of FIG. 1.

Continuing to refer to FIG. 2, the connection line 66 is connected to a programmable logic unit 58, which may be, e.g. a programmable computer, which is used to receive electrical command/gating signals from the magnetic resonance system 10 of FIG. 1 and to control the conversion of such electrical command/gating signals into optical command signals. In one embodiment, as depicted in FIG. 2, the programmable logic unit 58 is used to modulate a laser 60, such modulation in the laser's 60 light representing the converted command signal. The laser 60 may be, e.g., Sanyo's Laser Diode 785 nanometer, 25 milliwatt, part number DL4140-001. Additionally, the laser 60 is used to supply power through the catheter assembly 12 to the electronic assembly 28 of FIG. 1.

Referring to FIG. 2, the optical to electrical signal converter 52 component of the optical interface assembly 34 is used to convert the received optical signal into an electrical signal. The received optical signal may be a digital encoding of the original analog electrical signal from the coils 30 of FIG. 1, or may be analog signals representing said original electrical signal. Such analog signals may be, e.g. modulated signals in the range of about 10 mega Hertz to about 1,000 mega Hertz. The converted optical to electrical signal is then sent on to the magnetic resonance system's (10 of FIG. 1) signal input channel 22 of FIG. 1 via electrical connection 64. The optical signal received by the optical to electrical signal converter 52 originates as a picked up electrical signal induced in the coils 30 of FIG. 1 located in the distal end 16 of FIG. 1 of the catheter assembly 12. Said electrical signal is converted to an optical signal by the electronic assembly 28 of FIG. 1 located in the distal end 16 of FIG. 1 of the catheter assembly 12.

Additionally, the optical signal sent to the optical to electrical converter 52 may comprise a reference optical signal component in addition to the optically encoded received signal. Such reference signal component may be, e.g., a constant optical signal, or a saw-tooth signal. The reference component of the optical signal is used for calibration of the optical signals. The bending of the catheter assembly 12 as well as the electrical components used to generate the optical signals may introduce nonlinear effects into the produced optical signal. Such nonlinearities may be quantified by the introduction of said reference optical signal component. In the case where said reference optical signal is utilized, optical to electrical converter 52 contains means (not shown) for utilizing said reference optical signal to correct any nonlinearities induced into the received optical signal.

Continuing to refer to FIG. 2 and to the embodiment depicted therein, a power supply 56 is connected to all components of the optical interface assembly 34 which require power to operate. Power supply 56 may be, e.g., an AC to DC power converter connected to an external United States' standard 120 Volt 60 Hertz wall socket. Alternatively, power supply 56 may be a system of one or more batteries.

Figure 3:
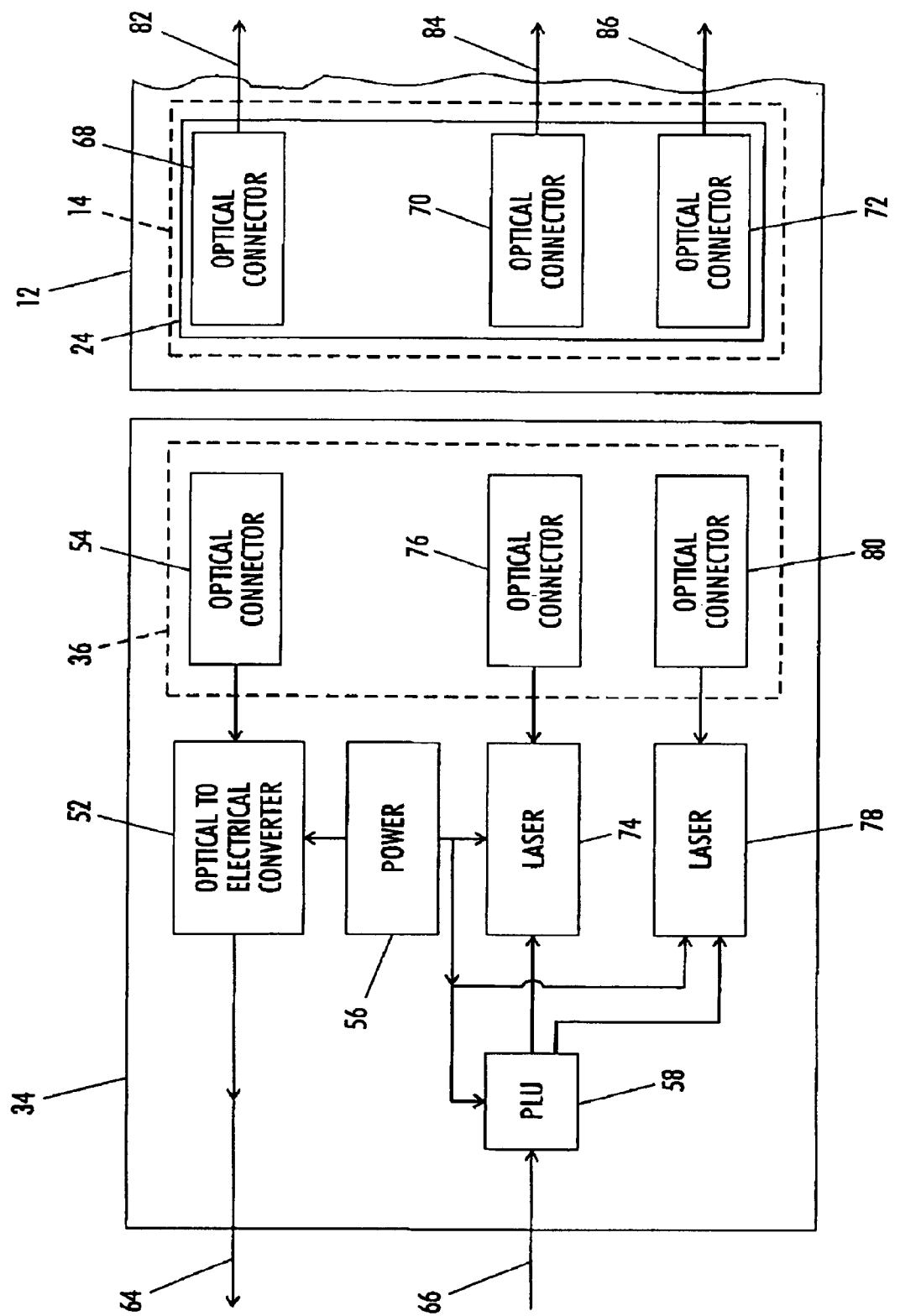
FIG. 3 is a block diagram of another Optical Interface component.

In another preferred embodiment, depicted in FIG. 3, three optical connectors 54, 76 and 80 are used to connect to the proximal end 14 of catheter assembly 12. Optical connectors 54, 76, and 80 are mated to optical connectors 68, 70, 72, respectively, in the connector assembly 24 of the proximal end 14 of the catheter assembly 12. In this embodiment, the fiber optic cable assembly 26 of FIG. 1 preferably is comprised of at least three optical fiber strands. Each strand 82, 84, 86 of the fiber optic cable assembly 26 of FIG. 1 services a different communication need.

Continuing to refer to FIG. 3, optical connectors 54 and 68 are used to connect the optical interface assembly 34 to the received signal strand 82 of the fiber optic cable assembly 26 of FIG. 1. Optical connectors 76 and 70 are used to connect the optical interface assembly 34 to the command signal strand 84 of the fiber optic cable assembly 26 of FIG. 1. Optical connectors 80 and 72 are used to connect the optical interface assembly 34 to the optical power transmission strand 86 of the fiber optic cable assembly 26 of FIG. 1. The optical power transmission strand 86 is used to deliver power to the distal end 16 of FIG. 1 of the catheter assembly 12 and in particular to the electronic assembly 28 of FIG. 1.

Continuing to refer to FIG. 3, the laser 74 is used to generate optical command/gating signals. These optical command/gating signals are used by the electronic assembly 28 of FIG. 1 to tune and/or detune and/or gate (connect/disconnect) and/or select the receiving coils 30. Laser 78 is used to generate optical power for use by the electronic assembly 28 of FIG. 1 in the distal end 16 of FIG. 1 of the catheter assembly 12. Both lasers 74 and 78 are controlled by the programmable logical unit 58 which may be, e.g. a programmable computer.

Figure 4A:
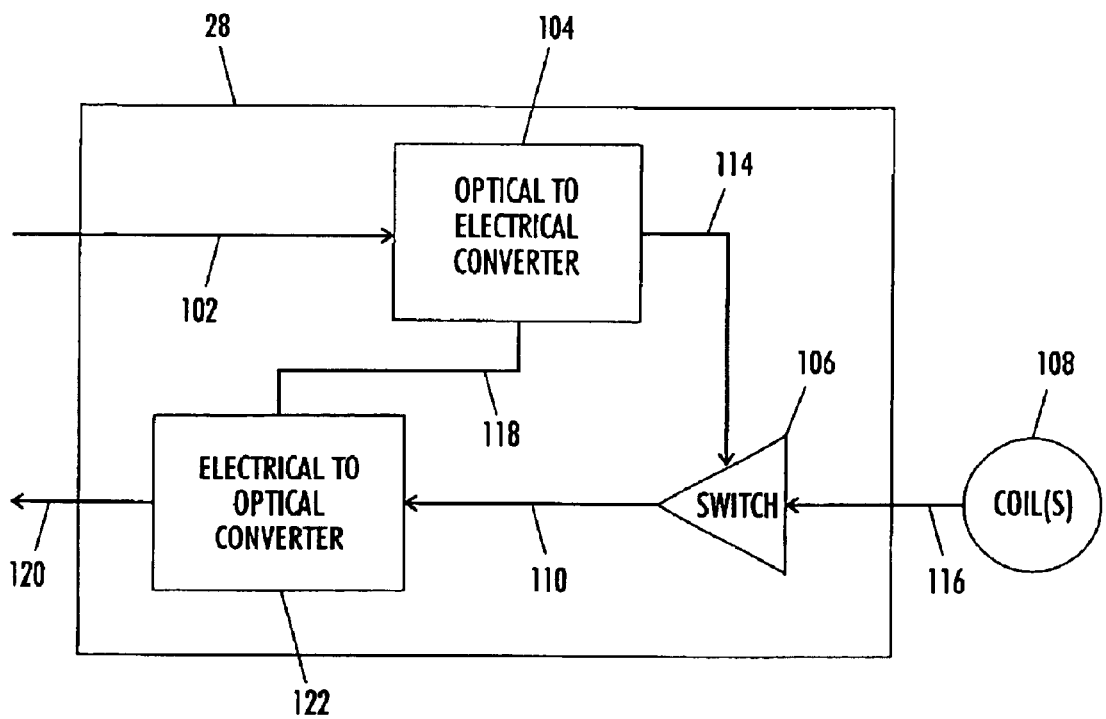
FIGS. 4 through 7 are component diagrams of the distal end of the catheter used in the device of FIG. 1.

Referring to FIG. 4A, and to the embodiment depicted therein, the components of the electronic assembly 28 of FIG. 1 are shown. An optical fiber strand 102 is connected to an optical to electrical converter 104, which is connected to a switch 106 via line 114. The optical to electrical converter 104 may be, e.g., a silicon photovoltaic cell. One such silicon photovoltaic cell can be UDT Sensors Inc.'s Planar Diffused Silicon Photodiode part number S-4CL. In one preferred method of operation, when a laser light is present at the optical to electrical converter 104, an electrical potential is applied to the switch 106, the switch 106 is open. In the absence of the laser light, and thus in the absence of an electrical potential, the switch 106 is closed.

Electronic assembly 28 also contains an electrical to optical converter 122 which converts the electrical signals received through the pickup coil(s) 108 into optical signals. Only when the switch is open may electrical signals from the coil(s) 108 reach the electrical to optical converter 122. The electrical to optical converter 122 is connected to the switch 106 via line 110 and to a fiber optic strand 120 of the fiber optic cable assembly 26 of FIG. 1. In one preferred embodiment, the electrical signals from receiving coils 108 are converted into digital optical signals. In another prefer embodiment, the electrical signals are converted into analog optical signals.

The coil(s) 108 are connected to the switch 106 via line 116. The coil(s) 108 may comprise electronic components, e.g. one or more capacitors, suitable to tune the receiving coil(s) 108 to a preferred electromagnetic frequency as well as to connect the coil(s) 108 to the electrical ground to prevent electrostatic charge from building up, as is known to those skilled in the art.

Figure 4B:
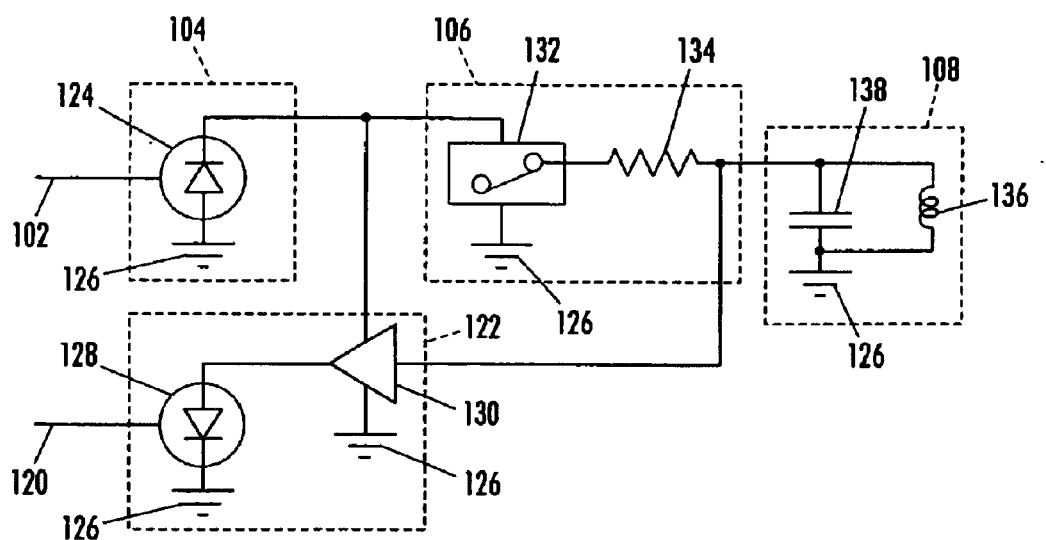

FIG. 4B illustrates one preferred electronic embodiment of the components shown in FIG. 4A. In this embodiment, the optical to electrical converter 104 consists of a silicon photovoltaic cell 124 and the catheter's common ground 126. The switch 106 comprises a normally closed switch 132, the catheter's common ground 126, and resistor 134. The electrical to optical converter 122 comprises a photodiode 128, the catheter's common ground 126, and a preamplifier 130. The coils 108 comprises a single inductive loop coil 136, a tuning capacitor 138, and the catheter's common ground 126. All such electronic components are well known to those skilled in the art.

Figure 4C:
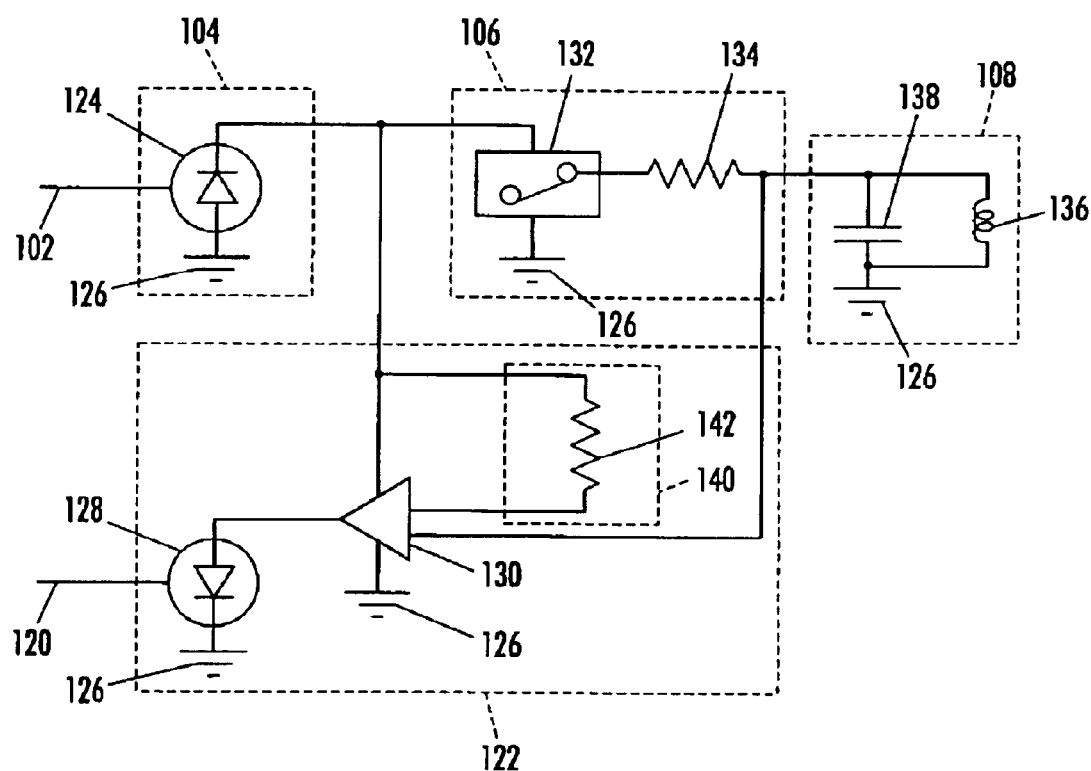

FIG. 4C illustrates another preferred electronic embodiment of the components shown in FIG. 4A. In this embodiment, the electrical to optical converter 122 further comprises a reference signal source 140 used to calibrate the received signal. In the embodiment depicted in FIG. 4C, the reference signal source comprises a resistor connected to the optical to electrical converter 104 and to the a preamplifier 130. In this arrangement, a constant signal is used for the reference calibration signal. The constant reference signal is added to the received signal. In another embodiment (not shown), a saw-tooth signal generator is used for the reference signal source 140.

In another embodiment, and continuing to refer to FIG. 4A, switch 106 is preferably a multi-state switch, used to select which of several coils 108 is to have their signals passed to the electrical to optical converter 122. The signal that the switch 106 receives from the optical to electrical converter 104 provides information indicating which of the coils 108 to connect to the electrical to optical converter 122. This is accomplished, e.g. by assigning different voltage levels to different receiver coils. For example, if the coils 108 consist of two different receiver coils (not shown), then the switch 106 is preferably a three state switch. Then an absence of any voltage from the optical to electrical converter 104 indicates the switch 106 is closed and that no receiver coil is connected to the electrical to optical converter 122. If a voltage between the range ¼ to ½ Volts is applied to the switch 106, then the switch 106 connects receiver coil #1 (not shown) to the electrical to optical converter 122. Finally, if a voltage between ¾ and 1 Volts is applied to switch 106 then the switch 106 connects receiver coil #2 (not shown) to the electrical to optical converter 122.

Figure 5:
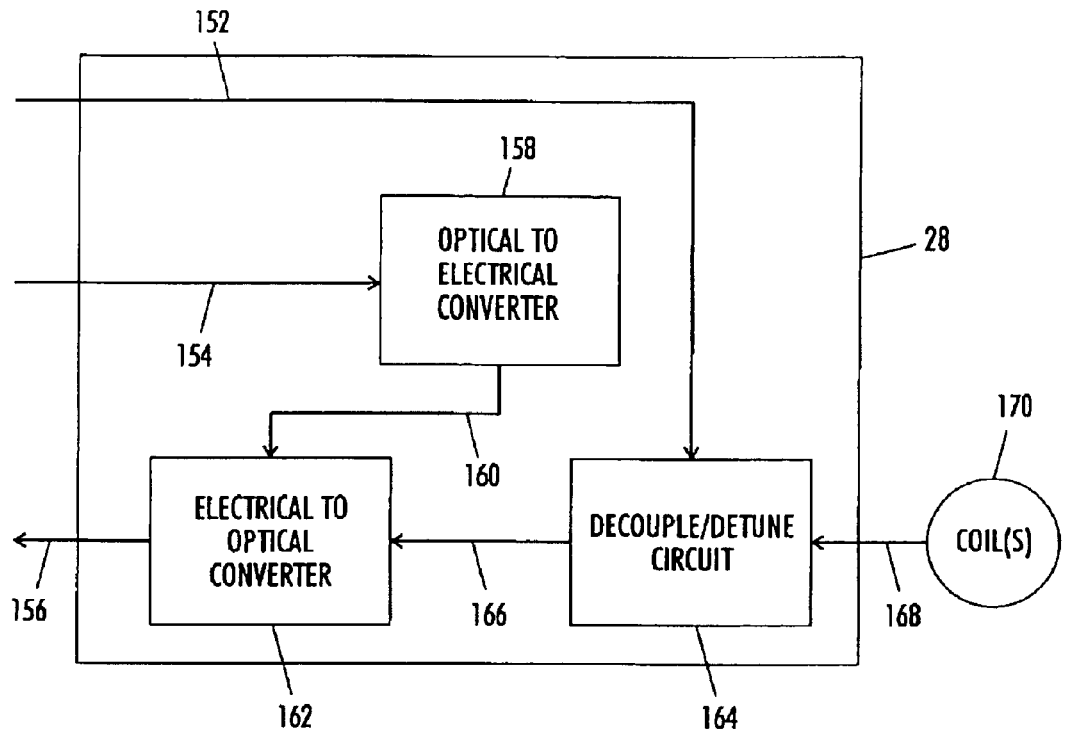

In another preferred embodiment, as depicted in FIG. 5, the electronic assembly 28 is connected to three fiber optic strands 152, 154, 156 of the fiber optic cable assembly 26 of FIG. 1. Additionally, the electronic assembly 28 is connected to the receiver coil(s) 170 via line 168.

Continuing with the preferred embodiment depicted in FIG. 5, the fiber optic strand 152 carries optical signals to the detuning assembly 164. The detuning assembly 164 may comprise, e.g. photo resistors and/or other optically active components so arranged and so connected to the receiver coil(s) 170 as to change the resonance frequency of the receiver coil(s) 170 depending on the presence or absence of light in said fiber optic strand 152. See, for example, the article "An Optical System for Wireless Detuning of Parallel Resonant Circuits" by E. Y. Wong, et. al., Journal Of Magnetic Resonance Imaging, 12:632–638 (2000) for one such detuning assembly. In another embodiment, detuning assembly 164 may comprise a switch activated by the presence or absence of a light in the optic strand 152.

Continuing with FIG. 5, the fiber optic strand 154 is used to deliver optical power to the optical to electrical converter 158. Optical to electrical converter 158 may comprise, e.g., a photovoltaic cell which converts the delivered laser light into an electrical potential difference suitable for powering other electronic components within the electronic assembly 28.

The optical to electrical converter 158 is connected to the electrical to optical converter 162 via line 160. The electrical to optical converter 162 is used to amplify and convert the electrical signal received in the coil(s) 170 into an optical signal and to transmit said optical signal through fiber optic strand 156. In one embodiment the optical signal sent through fiber optic strand 156 is a digital optical signal. In another embodiment the optical signal sent through fiber optic strand 156 is an analog optical signal.

In another embodiment, not shown, the optical to electrical converter 158 is further connected to the detuning component 164 to deliver electrical power to this component of the electronic assembly 28.

Figure 6:
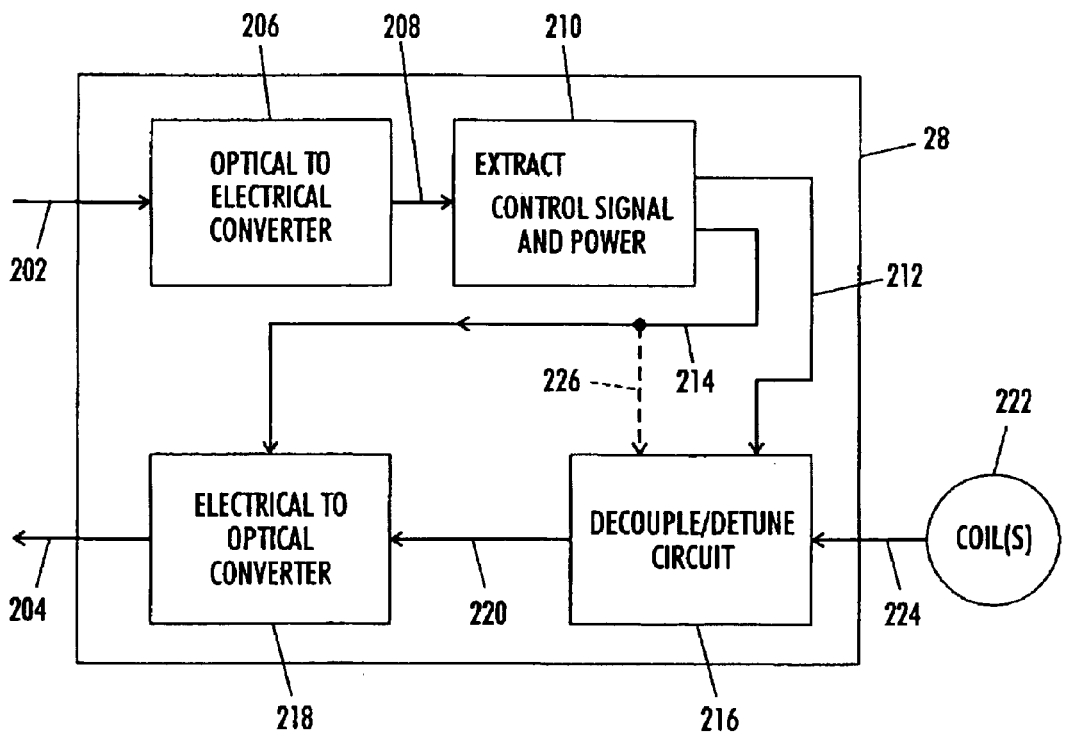

Referring to FIG. 6 and to the preferred embodiment depicted therein, the components of the electronic assembly 28 of FIG. 1 is shown. In this embodiment there are two fiber optic strands 202, 204 connecting to electronic assembly 28. Additionally, the receiver coil(s) 222 is connected to the electronic assembly 28 via line 224.

The fiber optic strand 202 carries a modulated laser light. This laser light is used to produce electrical power for the other electrical components in the electronic assembly 28 as well as to provided control signals suitable for controlling the decoupling circuit 216. The laser light traveling through fiber strand 202 is converted to an electrical signal by the optical to electrical converter 206. The optical to electrical converter 206 may comprise, e.g., a photovoltaic cell. The converted signal is passed on to the command extraction component 210 via line 208 where it is filtered for a detuning command as well as to provide power to other components within the electronic assembly 28. Any detuning command signals are sent to the decoupling component 216 via line 212. The power connection for the electrical to optical converter is provided by line 214. In one embodiment the decoupling component 216 may require electrical power. This be provided to it via optional line 226.

In one embodiment, the decoupling component 216 consists of a switch which is opened when a potential difference is provided to it via line 212 and is closed in the absence of a potential difference.

In one embodiment, the decoupling component 216 comprises at least one capacitor whose capacitance changes with the application of a potential difference. In this way, the signals from line 212 change the capacitance of the receiving coil(s) 222. Thus the coils are tuned and de-tuned to receive and/or not to receive signals in a predetermined frequency range. Additionally, by actively adjusting the capacitance, the catheter assembly 12 of FIG. 1 can be utilized with any of a number of different magnetic resonance systems 10 of FIG. 1, including systems utilizing 0.5 Tesla through 7.5 Tesla magnetic fields.

Continuing to refer to FIG. 6, when the receiving coils 222 are tuned to receive a signal, or in the case of switching when the switch is opened, the received signals are passed to the electrical to optical converter 218 via conducting line 220. The electrical to optical converter 218 is delivered power via line 214. The received signal is converted to an optical signal by the electrical to optical converter 218 which is in turn sends the optical signal through fiber optic strand 204. The electrical to optical converter 218 can comprise a preamp, a reference signal generator, and other electrical components.

Figure 7:
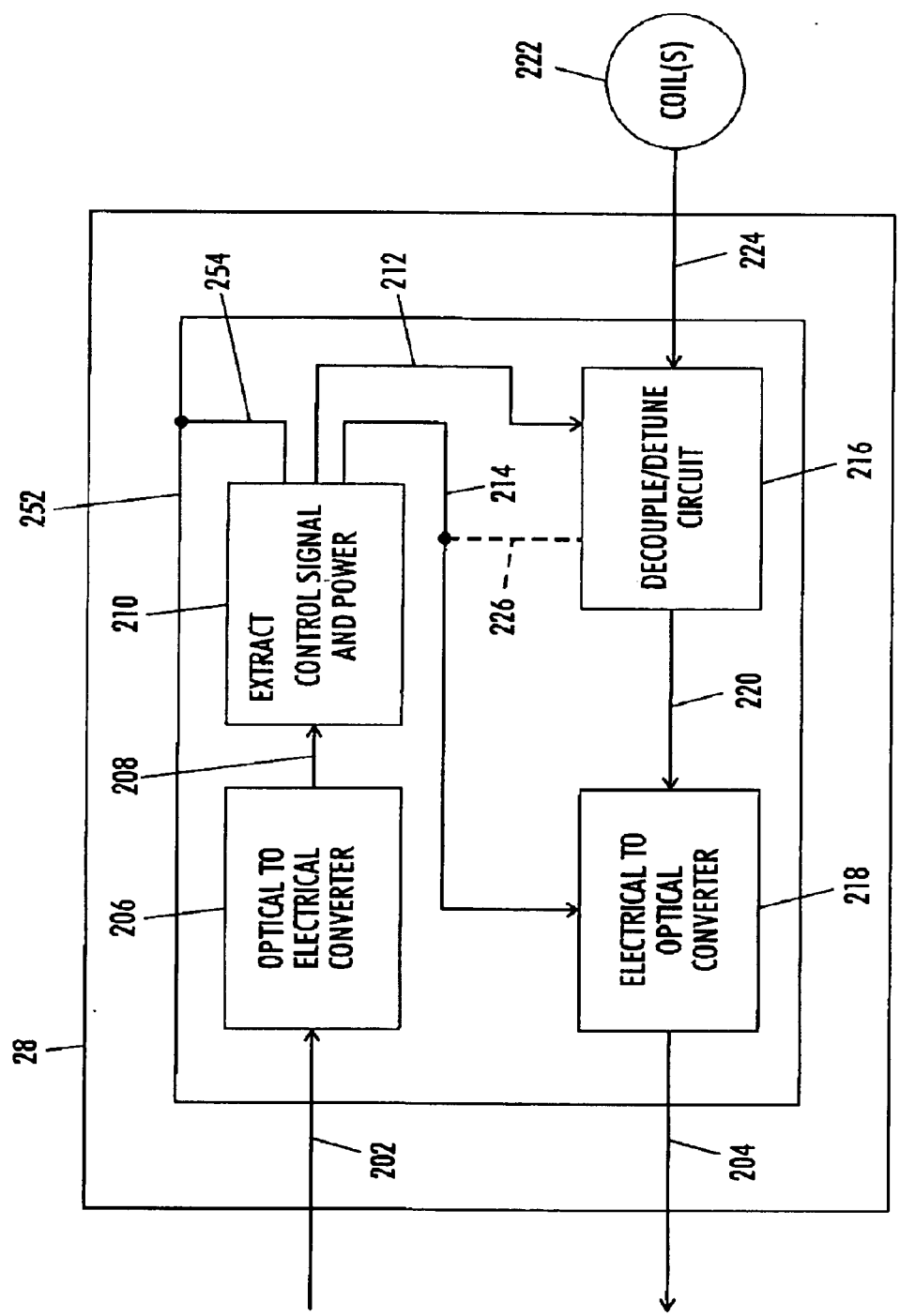

Referring to FIG. 7 and to the embodiment depicted therein, the electronic assembly 28 comprises electrical components, as in FIG. 6, contained within an electromagnetic shielding encasement 252. The electromagnetic shielding encasement 252 comprises a coating of nanomagnetic particulate material (not shown) so designed as to respond to an electrostatic or time-varying magnetic field or effect, in a manner similar to that of liquid crystal display (LCD) materials. More specifically, these nanomagnetic particulate materials (not shown) are designed to shift alignment and to effect switching from a magnetic shielding orientation to a non-magnetic shielding orientation when a voltage is applied. Signal and power extraction element 210 preferably has means for providing a voltage to the shielding encasement 252 via line 254.

In another embodiment (not shown), the electromagnetic shielding encasement 252 of FIG. 7 may comprise a Faraday cage.

In another embodiment (not shown), the electromagnetic shielding encasement 252 may comprise superparamagnetic material.

In another embodiment of this invention, catheter assembly 12 of FIG. 1 comprises additional means for allowing the positional tracking of the catheter assmbly's 12 distal end 16 during a magnetic resonance procedure, e.g. during a magnetic resonance imaging procedure. In this case, the catheter may be so manufactured as to have narrow rings (not shown), e.g. having a length from about 0.5 millimeter to about 1 millimeter, equally spaced along the length of the catheter assembly 12. The rings (not shown) may be of a material, (e.g. gadolinium or other appropriate material) or combination of materials known to those skilled in the art which are visible in a magnetic resonance images without significantly distorting the applied magnetic fields in the immediate vicinity of the receiving coil(s) or antenna 30.

Figure 8A:
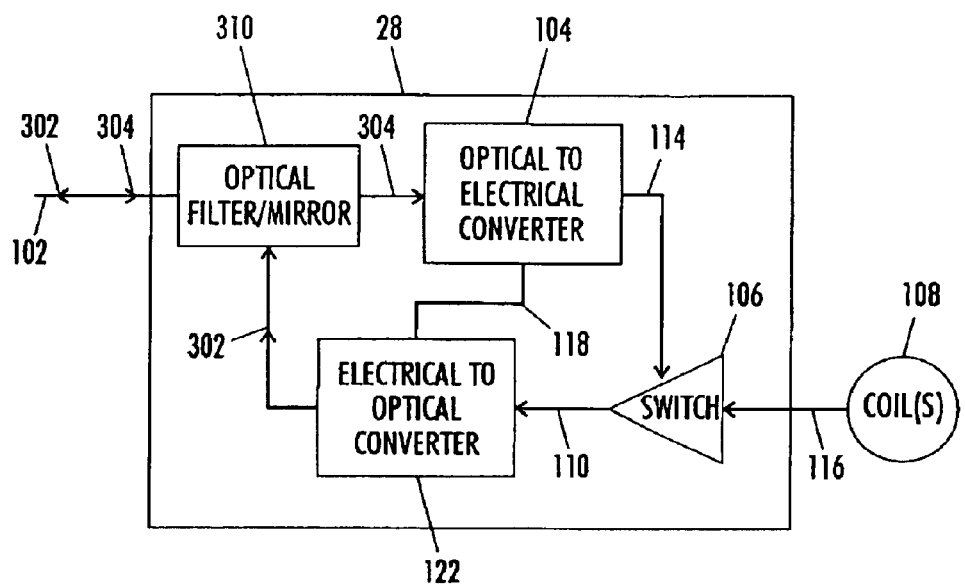
FIG. 8A is a block diagram of another design of the distal end of the catheter used in the device of FIG. 1.

In another preferred embodiment, as depicted in FIG. 8A, a single optic strand 102 is used for both transporting the optical command/gating signals 304 from the optical interface assembly 34 of FIG. 1 to the electronic assembly 28 as well as for transporting optical encoded signals 302 received from the coils 108 to the optical interface assembly 34 of FIG. 1. In this embodiment, and continuing to refer to FIG. 8A, an optical filter/mirror component 310 is added to the electronic assembly 28. The electrical to optical converter 122 receives an electrical signal 110 from the coil(s) 108 and converts it into an optical signal 302. Said optical signal 302 may be either a digital or an analog optical signal. Optical signal 302 is passed on to the optical filter/mirror component 310 which directs the optical signal 302 through the fiber optic strand 102. Optical signal 302 will have a fixed wavelength $\lambda_1$ while the optical command/gating signals 304 will have a different wavelength $\lambda_2$. The specific wavelengths to be used depends in part on the specific implementation of the optical filter/mirror 310.

Figure 8B:
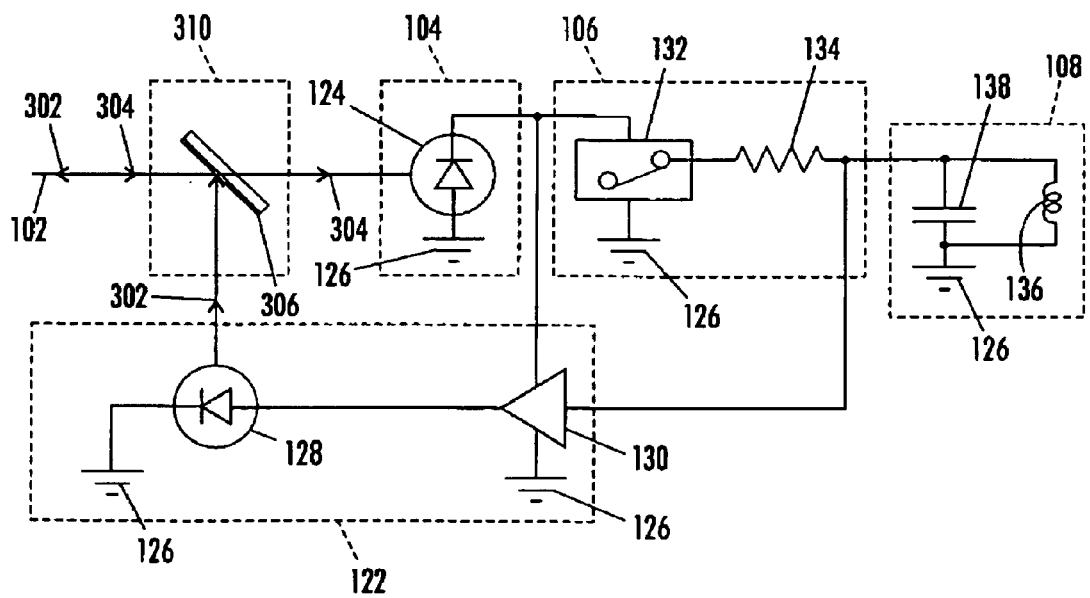
FIG. 8B is a schematic of the electronic components of the distal end.

FIG. 8B is a circuit diagram implementation for the embodiment depicted in FIG. 8A. Referring to FIG. 8B, and to the embodiment depicted therein, the optical filter/mirror 310 is implemented by element 306, which can be, e.g. a dichroic color filter, or a hot mirror, or a cold mirror. As is known to those skilled in the art, these optical elements are ready available for separating (reflecting and passing) and combining optical signals of different wavelengths. In one embodiment, optical filter/mirror 310 is a be a hot mirror 306 set at a 45 degrees angle to the incident optical signals 302 and 304 and which passes wavelengths, e.g., between about 450 nanometers to about 650 nanometers and reflects wavelengths, e.g., in the range of about 750 nanometers to about 1000 nanometers. Then wavelength $\lambda_1$ of optical signal 302 can be selected to be between 750 nanometers and 1000 nanometers so that optical signal 302 is reflected by hot mirror 306 while the wavelength $\lambda_2$ of optical signal 304 can be selected to be between 450 nanometers and 650 nanometers so that optical signal 304 is passed through hot mirror 306.

Figure 8C:
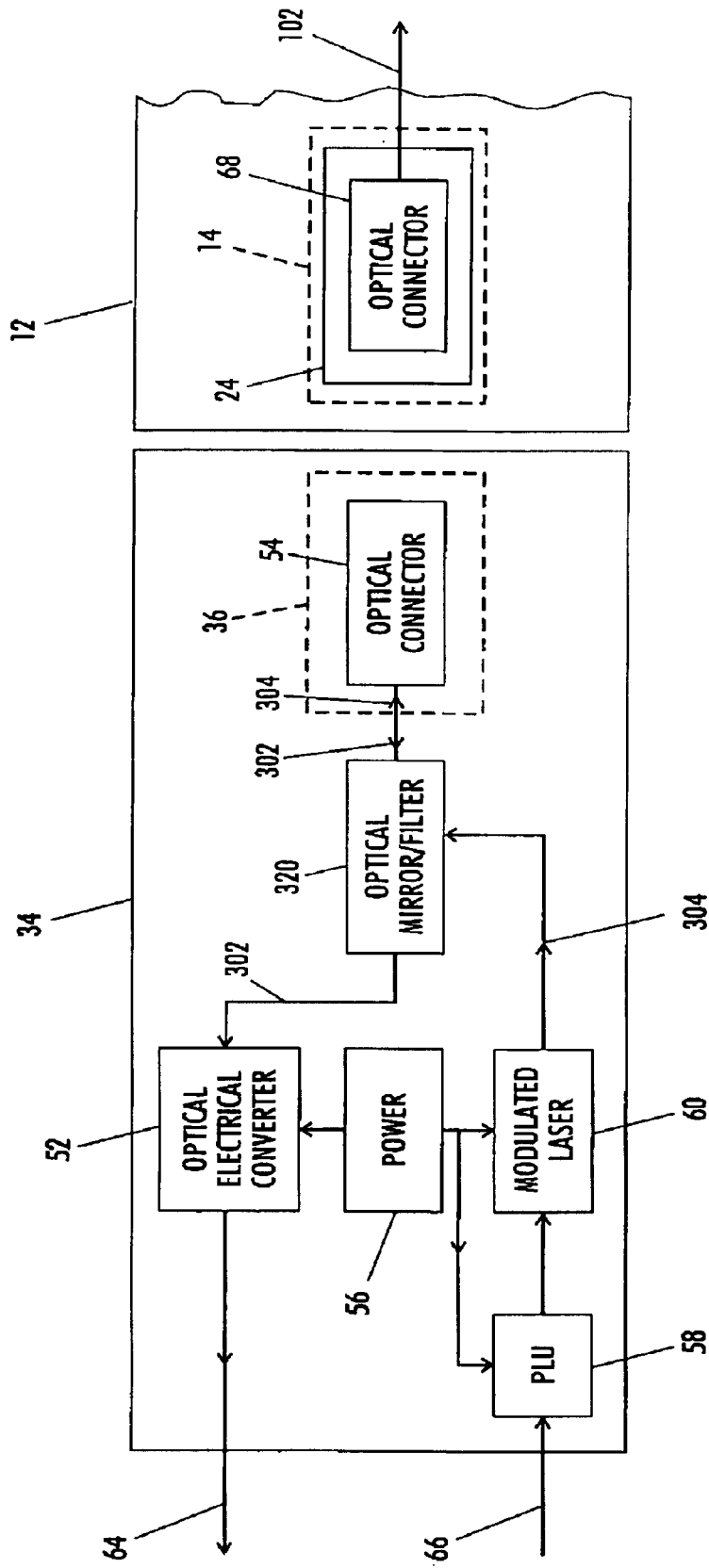
FIG. 8C is a block diagram of the Optical Interface wherein the catheter comprises a single optic strand.

FIG. 8C depicts the components for the optical interface assembly 34 for the case in which one optic strand 102 is used within the catheter assembly 12 for transporting both the magnetic resonance received signal 302 and the command/gating signal 304. In this embodiment, the optical interface assembly 34 comprises an optical mirror/filter which can be, e.g. a dichroic color filter, or a hot mirror, or a cold mirror. The optical signal 302 is passed through the optical mirror/filter to the optical to electrical converter 52, while the optical command gating/switching signal 304 from the modulated laser 60 is reflected by the optical mirror/filter 320 into the optical connector 54. In one embodiment, optical filter/mirror 320 is a cold mirror set at a 45 degree angle to the incident optical signals 302 and 304 and which reflects wavelengths, e.g., between about 450 nanometers to about 650 nanometers and passes wavelengths, e.g., in the range of about 750 nanometers to about 1000 nanometers. Then the wavelength $\lambda_1$ of optical signal 302 is preferably selected to be between about 450 nanometers and 650 nanometers so that optical signal 302 passes through cold mirror 320, while wavelength $\lambda_2$ of optical signal 304 is preferably selected to be between about 750 nanometers and 1000 nanometers so that optical signal 304 is reflected into optical connector 54 by cold mirror 306.

We claim:

1. An assembly for delivering optical signals, wherein said assembly is comprised of a nuclear magnetic resonance system, a optical interface assembly electrically connected to said nuclear magnetic resonance system, and a catheter assembly connected to said optical interface assembly, wherein:
   (a) said optical interface assembly converts optical signals into electrical signals; and
   (b) said catheter assembly is comprised of a fiber optic cable assembly, and an optical connection assembly at the proximal end of said catheter assembly, and an antenna disposed at the distal end of said catheter assembly, wherein said catheter assembly comprises means for converting electromagnetic signals received by said antenna into optical signals, and wherein said means for converting electromagnetic signals received by said antenna is disposed in said distal end of said catheter assembly.

2. The assembly as recited in claim 1, wherein said nuclear magnetic resonance system is a nuclear magnetic resonance imaging system.

3. The assembly as recited in claim 1, wherein said nuclear magnetic resonance system is a nuclear magnetic resonance spectrometer.

4. The assembly as recited in claim 1, wherein said catheter assembly is detachably connected to said optic interface assembly.

5. The assembly as recited claim 1 wherein said nuclear magnetic resonance system is comprised of a signal input channel.

6. The assembly as recited in claim 5, wherein said optical interface assembly is connected to said signal input channel.

7. The assembly as recited in claim 1, wherein said nuclear magnetic resonance system is comprised of a gating output channel.

8. The assembly as recited in claim 7, wherein said optical interface assembly is connected to said gating output channel.

9. The assembly as recited in claim 1, further comprising means for generating a calibration reference optical signal disposed in the distal end of said catheter assembly.

10. The assembly as recited in claim 1, wherein said fiber optic cable assembly is comprised of one strand of optical fiber.

11. The assembly as recited in claim 1, wherein said fiber optic cable assembly is comprised of a multiplicity of strands of optical fiber.

12. The assembly as recited in claim 1, wherein said fiber optic cable assembly is comprised of a hollow lumen.

13. The assembly as recited in claim 12, wherein said hollow lumen is a nonmagnetic, nonconductive hollow lumen.

14. The assembly as recited in claim 1, wherein said optical interface assembly is comprised of means for converting analog optical signals to electrical signals.

15. The assembly as recited in claim 1, wherein said optical interface assembly is comprised of means for converting digital optical signals to electrical signals.

16. The assembly as recited in claim 1, wherein said catheter assembly is comprised of means for converting electrical signals into analog optical signals.

17. The assembly as recited in claim 1, wherein said catheter assembly is comprised of means for converting electrical signals to digital optical signals.

18. The assembly as recited in claim 1, wherein said antenna is selected from the group consisting of a pickup coil, a single loop coil, a multi-loop coil, a loopless antenna, and a dipole antenna.

19. The assembly as recited in claim 1, wherein said catheter assembly is coated with a biocompatible material.

20. The assembly as recited in claim 19, wherein said catheter assembly is a magnetic resonance imaging intraluminal catheter.

21. The assembly as recited in claim 1, wherein said optical interface assembly is comprised of a programmable interface.

22. An assembly for delivering optical signals, wherein said assembly is comprised of a nuclear magnetic resonance system, an optical interface assembly electrically connected to said nuclear magnetic resonance system, and a catheter assembly connected to said optical interface assembly, wherein:
   (a) said optical interface assembly converts optical signals into electrical signals, and electrical signals into optical signals.
   (b) said catheter assembly is comprised of a fiber optic cable assembly, and an optical connection assembly at the proximal end of said catheter assembly, and an antenna disposed at the distal end of said catheter assembly, wherein said catheter assembly comprises means for converting electromagnetic signals received by said antenna into optical signals and comprises means for converting optical signals received from said optical interface assembly into electrical signals wherein said means for converting electromagnetic signals into optical signals and optical signals into electrical signals is disposed in said distal end of said catheter assembly.

23. The assembly as recited in claim 22, wherein said nuclear magnetic resonance system is a nuclear magnetic resonance imaging system.

24. The assembly as recited in claim 22, wherein said nuclear magnetic resonance system is a nuclear magnetic resonance spectrometer.

25. The assembly as recited in claim 22, wherein said catheter assembly is detachably connected to said optical interface assembly.

26. The assembly as recited claim 22 wherein said nuclear magnetic resonance system is comprised of a signal input channel.

27. The assembly as recited in claim 26, wherein said optical interface assembly is connected to said signal input channel.

28. The assembly as recited in claim 22, wherein said nuclear magnetic resonance system is comprised of a gating output channel.

29. The assembly as recited in claim 28, wherein said optical interface assembly is connected to said gating output channel.

30. The assembly as recited in claim 22, further comprising means for generating a calibration reference optical signal disposed in the distal end of said catheter assembly.

31. The assembly as recited in claim 22, wherein said fiber optic cable assembly is comprised of one strand of optical fiber.

32. The assembly as recited in claim 22, wherein said fiber optic cable assembly is comprised of a multiplicity of strands of optical fiber.

33. The assembly as recited in claim 22, wherein said fiber optic cable assembly is comprised of a hollow lumen.

34. The assembly as recited in claim 33, wherein said hollow lumen is a nonmagnetic, nonconductive hollow lumen.

35. The assembly as recited in claim 22 wherein said optical interface assembly is comprised of means for converting analog optical signals to electrical signals.

36. The assembly as recited in claim 22, wherein said optical interface assembly is comprised of means for converting digital optical signals to electrical signals.

37. The assembly as recited in claim 22, wherein said catheter assembly is comprised of means for converting electrical signals into analog optical signals.

38. The assembly as recited in claim 22, wherein said catheter assembly is comprised of means for converting electrical signals to digital optical signals.

39. The assembly as recited in claim 22, wherein said antenna is selected from the group consisting of a pickup coil, a single loop coil, a multi-loop coil, a loopless antenna, and a dipole antenna.

40. The assembly as recited in claim 22, wherein said catheter assembly is coated with a biocompatible material.

41. The assembly as recited in claim 22, wherein said catheter assembly is a magnetic resonance imaging intraluminal catheter.

42. The assembly as recited in claim 22, wherein said optical interface assembly is comprised of a programmable interface.

* * * * *